(12) United States Patent
Kittelmann et al.

(10) Patent No.: US 8,491,577 B2
(45) Date of Patent: Jul. 23, 2013

(54) SYSTEM FOR OPHTHALMIC LASER SURGERY

(75) Inventors: Olaf Kittelmann, Berlin (DE); Klaus Vogler, Eckental/Eschenau (DE)

(73) Assignee: Wavelight AG, Erlangen (DE)

( * ) Notice: Subject to any disclaimer, the term of this patent is extended or adjusted under 35 U.S.C. 154(b) by 949 days.

(21) Appl. No.: 12/471,952

(22) Filed: May 26, 2009

(65) Prior Publication Data
US 2010/0305553 A1 Dec. 2, 2010

(51) Int. Cl.
*A61F 9/01* (2006.01)
*A61B 18/20* (2006.01)

(52) U.S. Cl.
USPC .............................................. 606/5

(58) Field of Classification Search
USPC .............................................. 606/5
See application file for complete search history.

(56) References Cited

U.S. PATENT DOCUMENTS

| | | | |
|---|---|---|---|
| 5,748,222 A * | 5/1998 | Roberts | 347/241 |
| 2005/0165386 A1* | 7/2005 | Kurtz et al. | 606/4 |
| 2005/0197655 A1* | 9/2005 | Telfair et al. | 606/5 |
| 2007/0235543 A1 | 10/2007 | Zadoyan et al. | |
| 2008/0065052 A1* | 3/2008 | Bischoff et al. | 606/4 |
| 2008/0212623 A1 | 9/2008 | Bischoff et al. | |

FOREIGN PATENT DOCUMENTS

| | | |
|---|---|---|
| DE | 102005014760 A1 | 10/2006 |
| EP | 0770370 A2 | 5/1997 |
| WO | 2005058216 A1 | 6/2005 |

OTHER PUBLICATIONS

Patent Cooperation Treaty—European Patent Office, "Notification of Transmittal of the International Search Report and the Written Opinion of the International Searching Authority, or the Declaration," International Application No. PCT/EP2009/003730, Nov. 2, 2009, 13 pages.

* cited by examiner

*Primary Examiner* — Ryan Severson
*Assistant Examiner* — Rachel S Papeika
(74) *Attorney, Agent, or Firm* — Haynes and Boone, LLP

(57) ABSTRACT

The invention relates to a system for ophthalmic laser surgery, comprising a source (110) of pulsed laser radiation with radiation parameters matched to the making of an incision in an ocular tissue, particularly in the cornea, a scanner (160) for deflecting the laser radiation, an electronic control unit (190) which has been set up to control the scanner in accordance with a predetermined incision geometry, and a modulator unit (170) for modulating the laser pulses emitted from the source (110). The control unit (190) has furthermore been set up to control the modulator unit (170) in accordance with a beam-deflection pattern established for the incision geometry in such a manner that in predetermined parts of the beam-deflection pattern at least some of the laser pulses have a reduced pulse energy or are suppressed.

15 Claims, 4 Drawing Sheets

SYSTEM FOR OPHTHALMIC LASER SURGERY

Figure 1:
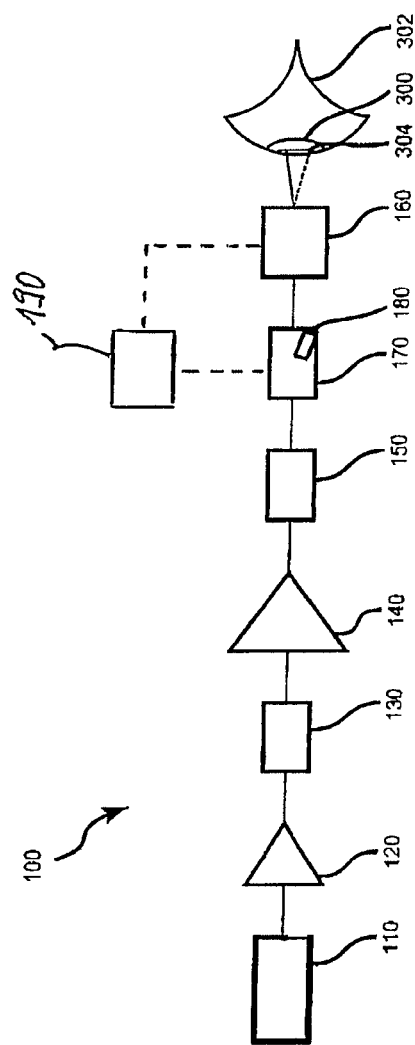

The invention relates to a system for ophthalmic laser surgery.

In refractive ophthalmic surgery the refractive properties of the eye are changed by interventions in respect of the eye of a patient for the purpose of correcting sight defects. In this connection the so-called LASIK process (LASer In-situ Keratomileusis) has great importance, wherein firstly a planar corneal incision is made, as a result of which a small cover disc—the so-called flap—arises. Said flap can be folded aside in order to expose the underlying corneal tissue, the stroma. Subsequently stromal tissue is ablated with a laser (commonly an excimer laser) in accordance with an ablation profile ascertained for the individual patient. After this, the flap is folded back; the wound heals up relatively quickly.

For the purpose of making the flap incision in the course of LASIK, the mechanical microkeratome used formerly has recently been replaced by an fs laser—that is to say, a laser that generates pulsed laser radiation with pulse durations within the femtosecond range. For an intra-tissue incision, the laser radiation has to lie within the transmissive wavelength range of the cornea—that is to say, above approximately 300 nm. At the same time, the energy density in the beam focus has to be great enough in order to generate an optical breakthrough, the so-called photodisruption. The effective region thereof is locally restricted to the focus diameter. In order to produce a flat incision, the beam focus must therefore be moved successively in accordance with a particular scan pattern onto a plurality of closely adjacent points, ordinarily overlapping one another, in the desired incision surface or incision plane.

The advantages of a laser incision, in comparison with a corneal incision that is made mechanically with a microscalpel, are resulting in an increasing spread of the use of femtosecond lasers in LASIK operations and other treatments in which incisions are to be introduced into the cornea.

When carrying out a flap incision by means of a femtosecond laser, in most cases the incision is obtained by a precisely defined alignment of closely adjacent femtosecond microdisruptions. In this connection the beam focus is guided, for example, along a meandering, serpentine path in the plane of the flap incision to be produced (so-called line scan). This cuts the so-called bed of the flap. Subsequently a final marginal incision is made along the desired edge of the flap. In this way the edge of the flap is defined.

The individual laser pulses are positioned precisely at the desired point in a plane (ordinarily designated as the x-y direction) that is normal to the beam direction, for example by means of a mirror scanner. As an alternative to a mirror scanner, use may be made of a crystal scanner, for example, in order to bring about the desired x-y deflection of the laser beam.

The quality of an incision to be made with fs laser radiation is influenced by the precise compliance with relevant parameters such as the pulse energy, the focus diameter, the focal plane and also the spacing of adjacent focal locations (spots). These parameters can be separately optimised well for various types of incision guidance. In the case of a flap incision, for example, a distinction can be made between two forms of incision guidance, namely the flap-bed incision—which cuts the flap bed and covers the latter, for example, by means of linear scan paths, largely arranged in parallel with alternating direction of motion—and the peripheral marginal incision which is frequently necessary for the detachment of the flap from the stroma.

The course of a scan path along which the laser beam is moved may sometimes not be optimal for the desired generation of an athermal (cold) photodisruption at each point along the scan path. Depending on the course of the path, local concentrations of the laser spots may occur. For example, in the case of a meandering line scan with which the bed of a flap is to be cut, in the region of the reversing bends of the individual line segments an accumulation of the spots per unit of length or unit of surface area may arise in comparison with the number of spots in the region of the rectilinear path segments. This accumulation or concentration is due to the inertia of the scanner—particularly when use is being made of a mirror scanner—at the turning-points where the scan direction is reversed. Adjacent focal points are then possibly no longer clearly separated from one another but are situated so closely together that thermal damage to the corneal tissue as a consequence of excessive local radiation of energy can no longer be ruled out. Nevertheless, for the remaining region of the flap—that is to say, the actual bed—the result of the incision with the chosen beam parameters may be optimal.

It is consequently an object of the present invention to create a solution in terms of apparatus that, when making incisions in ocular tissue by means of short-pulse laser radiation, enables the risk of undesirable thermal damage to the ocular tissue to be reduced.

For the purpose of achieving this object, the invention provides a system for ophthalmic surgery, comprising a source of pulsed laser radiation with radiation parameters matched to the making of an incision in an ocular tissue, particularly in the cornea, a scanner for deflecting the laser radiation, an electronic control unit which has been set up to control the scanner in accordance with a predetermined incision geometry, and a modulator unit for modulating the laser pulses emitted from the source. The invention provides that the control unit has been set up to control the modulator unit in accordance with a beam-deflection pattern established for the incision geometry, in such a manner that in predetermined parts of the beam-deflection pattern at least some of the laser pulses have a reduced pulse energy or are suppressed. The invention consequently takes as its starting-point the perception that along the scan path of a laser beam there may be regions in which, due to the course of the path, an increased area-specific energy input may arise, with otherwise constant radiation parameters. The invention counters the risk of thermal damage resulting from this by purposefully lowering, in predetermined regions of the scan path, the area-specific energy input by means of suitable energy modulation or blanking of selected laser pulses. The energy modulation or blanking may be applied to each pulse or only to some of the pulses in the path region in question. For example, it is possible to blank only every second, every third or generally every nth pulse in the path region in question. Blanking means that the laser pulse in question is totally blocked or suitably deflected and absorbed, so that substantially nothing from it reaches the ocular tissue. But, instead of a blanking (masking), an energy attenuation of selected pulses may also be undertaken, so that although the pulses in question reach the ocular tissue they do this with purposefully lowered pulse energy in comparison with the energy of the pulses that are situated in the remaining parts of the scan path. Such an energy reduction may be equally strong for all the pulses concerned in the path region—i.e. all the laser pulses concerned are substantially lowered to the same energy level—or the laser pulses concerned may be at least partly energy-modulated to differing degrees.

Irrespective of whether selected pulses are blanked or energy-modulated, along the entire scan path such radiation parameters as the repetition-rate of the laser pulses emitted from the source or/and the spot size (focus diameter) preferentially remain unchanged.

The control of the modulator unit by the control unit is expediently effected in location-dependent manner—i.e. depending on the location or the region along the scan path or along the beam-deflection pattern where the beam focus is presently located. Alternatively or in addition, the control may take place in connection with a velocity of the laser radiation relative to the ocular tissue, with a change of the stated velocity—that is to say, the acceleration—or with a pulse energy of the laser radiation.

In this way it is possible, depending on information concerning the laser-beam focus, to adapt the pulse energy emitted to the ocular tissue suitably. As mentioned, this may be done in location-dependent or position-dependent manner. Alternatively or in addition, a suitable modulation may be imposed, depending on a pattern of motion assigned to the beam-deflection pattern—such as, for instance, a velocity profile of the laser-beam focus—or, for example, depending on information that is made available by the scanner unit or other system components.

According to a preferred embodiment, the beam-deflection pattern includes a serpentine pattern with a plurality of line paths extending rectilinearly side by side and with a plurality of reversing bends each terminally connecting a pair of adjacent line paths. In this connection the control unit has been set up to control the modulator unit in the region of at least some of the reversing bends for an energy reduction and/or a blanking of at least some of the laser pulses.

In the case of a beam-deflection pattern of such a type, which is composed of a plurality of straight line paths extending side by side substantially in parallel, a reversal of the direction of motion by about 180° takes place at the marginal regions of the incision geometry. At these points of the beam-deflection pattern, which are designated here as reversing bends, a retardation of the scan velocity arises by reason of an inertia which is inherent in the scanner. Given a substantially constant repetition-rate of the laser source—i.e. given a substantially constant pulse-rate of the laser radiation—in the case of a reduction of the scan velocity an increased energy input into the ocular tissue per unit of surface area results. A blanking of individual pulses or of entire pulse trains, brought about by the control unit, and/or a reduction in the energy of the individual pulses in the region of the reversing bends, may counteract harmful thermal loading possibly resulting from the increased energy input.

A flat incision can be produced not only with a meandering line scan but also with a so-called spiral scan. In this case the focus is moved along a spiral path. Given constant pulse repetition rate and constant angular velocity of the rotational beam deflection, the path spacing between consecutive focal locations is reduced towards radially inner branches of the spiral path. This corresponds to an increased energy input per unit surface area. For the purpose of avoiding any possible thermal damage which may arise by virtue of such an increased energy input, another preferred embodiment provides that the beam-deflection pattern includes a spiral pattern, the control unit having been set up to control the modulator unit for an energy reduction and/or a blanking of at least some of the laser pulses towards radially interior branches of the spiral pattern. By suitable energy reduction or blanking of pulses, in the interior parts of the spiral scan it is possible to avoid an excessive increase in the energy input per unit of surface area, so that a purely non-thermal photodisruption of the ocular tissue continues to be possible without concomitant thermal damage. It will be understood that a variation of the pulse repetition rate is not intended to be ruled out, and may be implemented in addition to an energy modulation of the pulses.

Overall, a meandering linear incision guidance offers the advantage of a considerably more freely selectable incision geometry in comparison with a spiral scan. The preparation of an elliptical flap incision—as is indicated, for example, in the case of an astigmatism—can be realised with a spiral-shaped incision guidance with approximately uniform surface density of the microdisruptions only with increased control effort.

One embodiment provides that the modulator unit includes an optical grating component with variable diffraction efficiency. The diffraction brought about by the grating component either may blank the laser beam completely—by, for example, completely deflecting it into a beam dump which is optionally present—or may diffract only parts of the beam out of the beam path and in this way reduce the energy brought onto or into the ocular tissue by the beam.

The modulator unit preferably includes an acousto-optical or electro-optical modulator. With a modulator of such a type, the laser radiation can be interrupted, for example, very quickly and over a defined short time-interval, in order to avoid an undesirable local superposition of several laser-radiation pulses at the same location. Alternatively, instead of an interruption of the laser radiation or a blanking of individual or several laser pulses, a purposeful adaptation of the laser-radiation power or pulse power may be undertaken. In other words, instead of an (idealised) keying/blanking, corresponding to a switch with two positions, by virtue of the variation of the diffraction efficiency by means of the modulator a plurality of control positions as regards the diffraction efficiency, and hence ultimately also the energy emitted to the ocular tissue, can be taken up. In this connection, various functional linkages may be provided, for example between the diffraction efficiency and the location of the beam focus, the instantaneous velocity of the beam focus or the change in the beam-focus velocity—i.e. the acceleration.

The control unit may have been set up to control the modulator unit in such a manner that in at least one predetermined section of the beam-deflection pattern said modulator unit blanks each of several laser pulses situated in this section or reduces the pulse energy of each of these pulses compared with the pulse energy in other sections of the beam-deflection pattern. Alternatively or in addition, the control unit may have been set up to control the modulator unit in such a manner that in at least one predetermined section of the beam-deflection pattern said modulator unit blanks, alternately in succession, at least one first laser pulse or reduces the pulse energy thereof and leaves unchanged the pulse energy of at least one second laser pulse compared with the pulse energy in other sections of the beam-deflection pattern.

Figure 2:
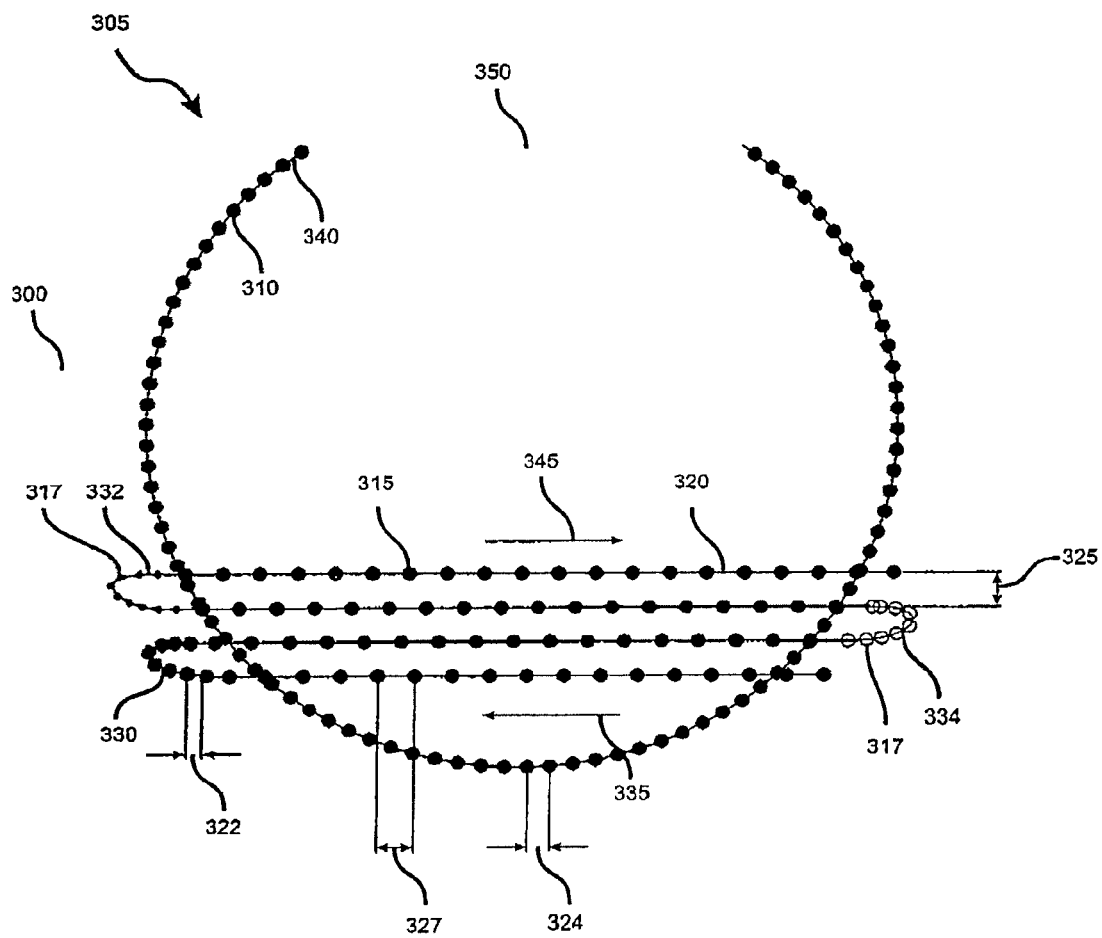
Figure 3:
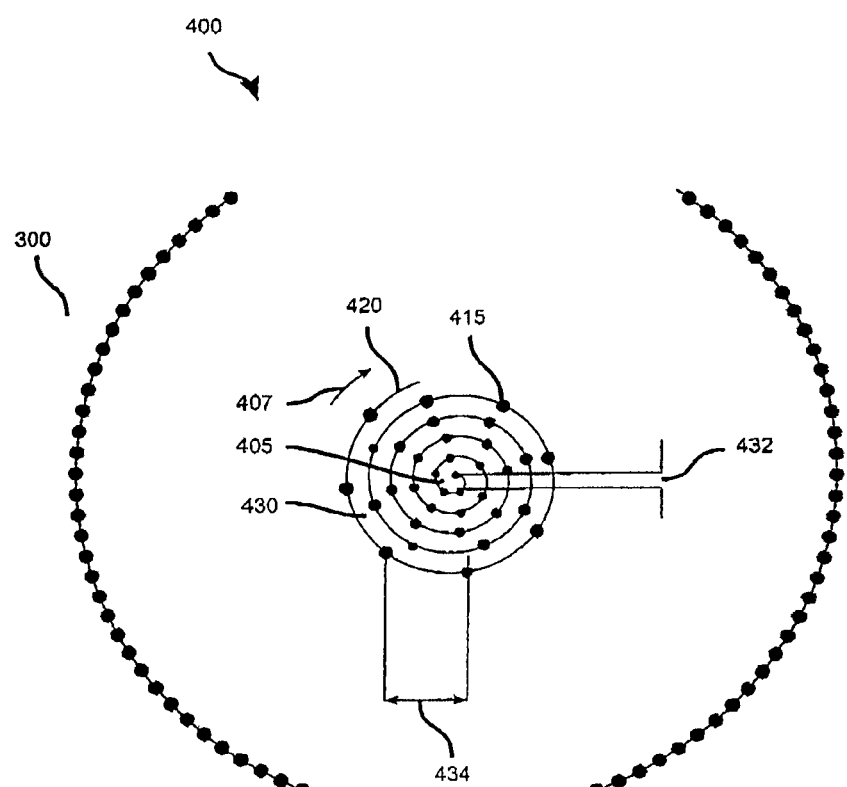
Figure 4:
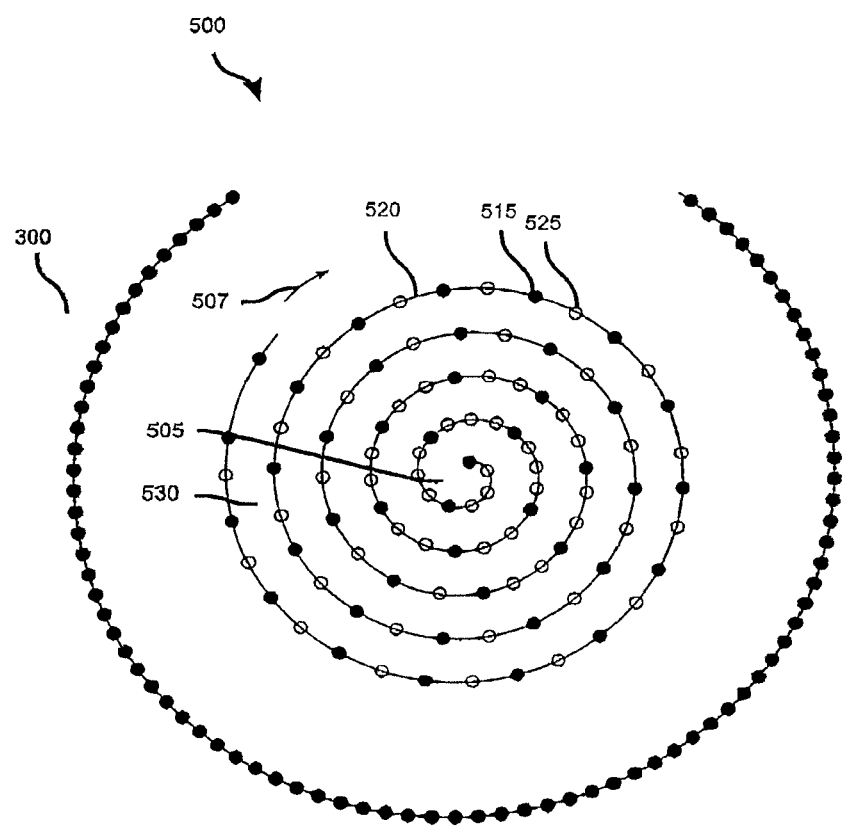

The invention will be elucidated in more detail in the following on the basis of the appended drawings. Represented are:

FIG. 1: a schematic exemplary embodiment of a system according to the invention for ophthalmic laser surgery, FIG. 2: a first exemplary scan pattern for a flap incision, FIG. 3: a second exemplary scan pattern for a flap incision and FIG. 4: a third exemplary scan pattern for a flap incision.

The system shown in FIG. 1 in schematic block representation, denoted generally by 100, is a laser system that is suitable for the production of an intra-tissue incision in the eye of a patient. An intracorneal flap incision for producing a LASIK flap is one possible and preferred example of an incision for which the laser system 100 is suitable. However, it is not excluded to produce other forms of a tissue incision in the eye with the laser system 100.

The laser system 100 includes a laser oscillator 110 which, in free-running manner, emits laser pulses with a duration within the femtosecond range and at a defined repetition-rate. The laser oscillator 110 may, for example, be a solid-state-laser oscillator, in particular a fibre-laser oscillator. The pulses emitted by the laser oscillator 110 pass through a preamplifier arrangement 120 which increases the power of the pulses. At the same time, the preamplifier arrangement 120 brings about a temporal stretching of the pulses. The laser pulses that have been pretreated in such a way are then reduced in their repetition-rate by means of a so-called pulse picker 130. The laser oscillator 110 provides, for example, pulses at a rate of 10 MHz or more. This rate is reduced to, for example, 200 kHz with the aid of the pulse picker 130. The pulses that have been reduced in their repetition-rate in such a way are input to a power amplifier 140 which generates the pulse energy of the still temporally extended pulses that is needed for the application. Before the pulses that have been amplified in this way are supplied to a final pulse compressor 150, they ordinarily have a pulse length of over one picosecond, which is again compressed by the final pulse compressor 150 to the short fs pulse width, made possible by the bandwidth of the oscillator 110 and of the amplifier media, of, for example, below 500 fs. In the case of the final pulse compressor 150, it may be a question, for example, of a grating compressor.

Components 110, 120, 130, 140 and 150 may be regarded, taken together, as a laser source in the sense of the invention.

The succession of fs laser pulses generated in this way subsequently passes through a pulse modulator 170 which, for example, takes the form of an acousto-optical modulator or an electro-optical modulator. Generally the pulse modulator 170 may contain arbitrary optically active elements which enable a rapid blanking or modulation of the energy of the laser pulses. An acousto-optical modulator may, for example, offer switching-times from less than 10 µs down to, for example, 2 µs, with an off-time of approximately 10 µs to 100 µs.

Assigned to the pulse modulator 170 in FIG. 1 is a beam dump 180 which serves to absorb any possible pulses to be blanked that are not to reach the target to be treated. Such pulses to be blanked can be deflected by the pulse modulator 170 onto the beam dump 180, so that they are no longer contained in the further beam path of the laser beam directed onto the target.

Downstream of the modulator 170 the laser beam reaches a scanning and focusing arrangement 160 which is represented schematically here as a common block and which deflects the laser beam in a plane (x-y plane) perpendicular to the beam direction in accordance with a predetermined scan pattern or beam-deflection pattern and focuses it onto the desired destination in the beam direction (z-direction). In the case of an eye treatment, the destination is situated in the ocular tissue and, in particular, in the corneal tissue. For the consecutive laser pulses the beam-deflection pattern defines the position of each pulse in the x-y plane. In other words, it establishes a path (or several paths), along which the laser beam is to be moved, in order ultimately to obtain the desired incision.

The scanning and focusing arrangement 160 may, for example, include an x-y mirror scanner with two galvanometrically operated deflecting mirrors, which are capable of swivelling about mutually perpendicular axes, for the beam scanning, and an f-theta objective for the purpose of beam focusing.

The pulse modulator 170 and the scanning and focusing arrangement 160 are coupled with a program-controlled control unit 190. The latter contains, in a program memory which is not represented in any detail, a control program which upon execution by the control unit 190 brings about such a control of the pulse modulator 170 and of the scanning and focusing arrangement 160 that the laser beam is focused in the desired target plane, is moved over the target plane in a manner corresponding to the desired beam-deflection pattern, and, in predetermined parts of the beam-deflection pattern which are defined in the control program, at least some of the laser pulses are attenuated in energy by the pulse modulator 170 or are blanked completely.

In the exemplary case that is shown, the laser beam that is output by the scanning and focusing arrangement 160 is directed onto a cornea 300 of a human eye 302 and is guided there with its focus in an intracorneal (planar or non-planar) incision plane 304. This incision plane 304 is represented as a line in the present stylised sectional representation of the eye 302. A detailed elucidation of the incision guidance and also of the mode of operation of the modulator 170 in connection with the incision guidance results from the following description of FIG. 2.

FIG. 2 shows a detail of the human cornea 300 on which a flap incision according to a first flap-incision schema 305 is to be carried out. The flap-incision schema 305 is only represented schematically; in particular, under certain circumstances the size ratios do not correspond to the real ratios. In addition, the flap-incision schema 305 is indicated only partially, in order to keep the representation as a whole clearly comprehensible.

For the purpose of carrying out the flap incision, laser pulses are focused at points 310, 315 of the cornea 300 which are illustrated by circles, so that microdisruptions arise. The laser radiation generated by the system 100 is guided over the surface of the cornea 300 by means of a high-speed scanner. As a rule, the cornea exhibits a surface curvature which may be designated, in a first approximation, as spherical. For the implementation of a flap incision, it is, for example, conventional to level the surface of the cornea to be treated by pressing on or suctioning on an attachment. The focusing of the femtosecond laser radiation is effected within a plane 304 (see FIG. 1) which extends substantially perpendicular to the visual axis of the eye, so that a substantially uniform flap thickness arises. The laser beam is guided within this plane along defined path curves.

In a first part of the incision schema 305 the planar flap-bed incision is produced. To this end, the laser beam is guided along a substantially straight scan path 320 in a first direction of motion 335 and, upon exceeding the desired flap-incision radius, changes its direction of motion to a second direction of motion 345 and is subsequently again guided along a straight line parallel to, and with a defined spacing 325 from, the first scan line 320, so that the entire surface of the flap incision is scanned in the form of a grid or in meandering form with alternating directions of motion 335, 345.

Within the individual scan lines 320 the focal locations 315 are aligned with one another in virtually equidistant manner with a spacing 327, since pulse-rate and scan velocity along the lines 320 are kept constant. The individual scan lines 320 are provided with a spacing 325 from one another in such a way that, together with the spacing 327 of the individual focal locations 315 within the scan line, on the whole a two-dimensional incision arises. At the margins within the reversing bends 330 of the flap-incision pattern the direction of motion of the laser beam changes, for example by approximately 180°. At these reversing bends 330 a retarded relative velocity between laser beam and corneal surface results by reason of the inertia of the scanner, so that many of the focal locations 315 are situated locally close together or coincide. This is evident in a distinctly smaller focal-location spacing 322 within the reversing bends 330 compared with the focal-location spacing 327 along the scan-route sections 320. These regions 330 are consequently subject to potential thermal damage.

For the purpose of completing the flap incision, after the surface incision represented by the lines 320 a marginal incision along a, for example, substantially circular path 340 is carried out. For the marginal incision a different focus density may be required or advantageous, compared, for example, with that of the flap-bed incision. Correspondingly, the spacing 324 of the focal locations 310 along the marginal-incision path curve 340 in the exemplary embodiment shown in FIG. 2 is smaller than the spacing 327 of the focal locations along the substantially linear path curves 320. The marginal incision 340 is interrupted at a point 350 which serves as a (flap) hinge in the course of detaching the severed corneal region and folding it upwards. In the course of folding upwards, the potentially thermally damaged regions 330 along the line 340 are severed and are then situated outside the flap.

A first possibility, according to the invention, in order to reduce the aforementioned thermal damage at the reversing-points 330 consists in interrupting the emission of the laser radiation to the cornea by means of a suitable drive of the acousto-optical modulator 170 if the focal locations fall outside the (initially imaginary) marginal-incision line 340.

This situation is represented at the reversing bend 334. Those focal locations 315 and the associated microdisruptions which in region 334 would, respectively, fall on the cornea 300 and be triggered are represented as circles that have not been filled in. In this exemplary embodiment the laser-beam path through the modulator 170 is blocked in a region outside the edge of the flap, so that no pulses impinge on the cornea 300. But it is also conceivable that only single laser pulses or entire series of pulses are blocked. This blanking of laser pulses may be effected, for example, in a manner depending on a location signal, velocity signal or acceleration signal made available by the scanner unit 160. But, where appropriate, the generation and/or provision of signals may also be effected by other modules or components which are independent of the scanner unit. Furthermore, the blanking may, where appropriate, also be effected by a purely temporal control or programming of the laser-beam guidance or by taking other suitable signals into account. By virtue of this measure, as can be discerned in FIG. 2, the marginal region 334 is kept totally free from micro-disruptions induced by the laser beam, and thermal damage in this region is ruled out.

One strategy for avoiding thermal damage—which may be employed alternatively or, where appropriate, in combination with the possibility presented above—consists in a modulation of the energy of individual femtosecond pulses in the course of guidance of the incision in the cornea. This is represented in the reversing region 332 in FIG. 2. Instead of, as in region 334, keeping the local density of the individual focal locations on statistical average substantially approximately within a desired range, in region 332 the energy is reduced that is emitted to the cornea by the individual laser pulses in the form of the focal locations 317 by way of microdisruptions. For the purpose of representation, the circles that represent the focal locations of the laser radiation are represented as circles 317 with a smaller radius. For the purpose of obtaining a lower emission of energy, the acousto-optical modulator 170 is not switched from an on-state into the absolute off-state. Rather, in principle, for each pulse of the train of femtosecond pulses individual pulse energies are capable of being set which can be adapted to the concrete application in magnitude and succession. In this connection, switching-times can be realised that can modulate individual impulses at a repetition-rate of up to about 1 MHz. In the present case, for pulses that lie outside the flap-incision region a constantly lower pulse energy is set or adjusted. But a pulse-energy progression is also conceivable that is adapted to the presumable or actual velocity progression or acceleration progression. Moreover, it is conceivable to arrange the reversing bend 332 not outside the flap bed but rather within the marginal incision, and in this way to obtain a temporal shortening of the entire flap-incision procedure by dispensing with scanning beyond the actual marginal-incision region. With the flap-incision schema 305 represented in FIG. 2 it is possible for arbitrary flap shapes to be realised, which may be an advantage, in particular, in the case of higher-order aberrations of the corneal geometry, such as astigmatism for instance.

Another alternative form of production of a flap incision is represented in FIG. 3. Instead of a linear, meandering scanning of the flap-incision region, in the case of the flap-incision schema 400 shown in FIG. 3 a spiral scan guidance is provided. The representation of the incision schema is again only schematic—i.e. the size ratios and spacing ratios are, as in FIG. 2, not true to scale and may differ in reality from the schema that is represented. Furthermore, also as in FIG. 2 the incision guidance is incomplete. In particular, in the peripheral region of the spiral incision yet further pulses have to be positioned in the course of a real incision guidance.

In the present exemplary embodiment the incision guidance is effected along a spiral path 420 evolving outwards from the central region 405 of the cornea 300 to peripheral regions 430—in the present case, clockwise along the direction of motion indicated by an arrow 407 in FIG. 3. The individual focal locations 415 are placed along the spiral path 420 with continuous pulse-rate. The velocity profile generated by the scanner along the spiral path 420 is composed of a linear radial component as well as a rotational-speed component. In the case of a constant rotational component (i.e. constant angular velocity) and a constant radial component, given a constant pulse-rate in the central region 405 a distinctly higher focal-location density prevails along the path curve 420 than in peripheral regions 430, since in the peripheral region 430 the path velocity is higher by reason of the constant rotational speed. This is evident in a smaller focal-location spacing 432 in the central region 405 compared with the focal-location spacing 434 in the peripheral region 430.

Although the flap-incision schema 400 has the advantage that—in the case of the direction of motion 407 that has been described, from the centre 405 to the peripheral regions 430—the flat flap-bed incision can be transformed continuously into the flap-edge incision, on the other hand there is the risk of thermal damage in the central region of the cornea 300, which may be a particular disadvantage there. Also in the case of an evolution of the spiral path in the opposite direction of motion—i.e. from the peripheral edge region 430 of the flap inwards into the central region 405—there is the same risk, since here too use has to be made of a mixed pulse power which has a tendency to be too low for the peripheral region 430, given temporally fixed pulse frequency, and which in the central region 405 of the cornea 300 is possibly too high.

In order to achieve a more uniform energy input per unit of surface area, according to one embodiment of the invention the energy emitted to the ocular tissue of the cornea 300 at the focal locations 415 is modulated in such a manner that the energy input is lower in the central region 405 of the cornea than in the peripheral region 430. This is indicated in FIG. 3 by a radius of the circles representing the focal locations 415 which increases from the central region 405 to the peripheral region 430. Consequently, although the focal-location density is reduced from the inside 405 to the outside 430, by virtue of the increasing pulse power the energy input per focal location which is brought about by the triggered microdisruptions is higher and consequently compensates the reducing focal-location density to give an energy input per unit of surface area that remains substantially constant within a desired range. This compensation by means of the modulator 170 can be temporally controlled by a control unit in accordance with a previously established mathematical function; but a control loop may also be set up which regulates the pulse power, for example in a manner depending on the radial position of the scan device 160.

As an alternative to a control or regulation of the pulse power along the spiral-path curve 420, in the case of a spiral-path-scan schema a constant pulse density along a path curve can be adjusted by blanking of laser pulses. This is represented schematically in FIG. 4. For the purpose of avoiding repetition, in the description of FIG. 4 only the essential differences from the embodiments already described, shown in FIGS. 2 and 3, will be considered. In FIG. 4 a flap-incision schema 500 comparable to the schema of the embodiment shown in FIG. 3 is represented. By means of a spiral beam-deflection pattern along a path curve 520, this schema produces a flap-bed incision by applying laser pulses 515. In order to keep the focal spacing of the laser pulses 515 in the path curve 520 of the spiral scan substantially constant, by blanking of individual laser pulses 525 (instead of a variation of the pulse-repetition frequency of the laser source, or instead of a variation of the laser-pulse energy) the pulse-rate of the laser radiation impinging on the ocular tissue is changed continuously in accordance with the following equation $$s_f = const \sim \frac{d_i}{f_i} \ldots \frac{d_0}{f_0} f_i << f_0 \text{ as } d_i << d_0$$

where
$f_i$=pulse-rate in the inner spiral region;
$f_o$=pulse-rate in the outer spiral region;
$s_f$=spot spacing in the path curve;
$d_i$=diameter of the path curve in the central region;
$d_o$=diameter of the path curve in an outer region.

Consequently, an approximately uniform focal-location density over the entire flap-bed-incision region of the cornea 300 results by virtue of a blanking of three out of four pulses in a central region 505 and by blanking every second pulse in a peripheral region 530. The numerical values and size ratios represented here are, under certain circumstances, not true to reality or true to scale and serve only for schematic representation. In a concrete embodiment the actual pulse-to-blanking ratios may differ considerably from the values that are represented in simplified manner.

Overall, the local accumulation or even superposition—which is associated with negative consequences—of several fs laser pulses in the region of the reversing-points in the case of a linear grid-like flap-incision process or a too dense succession of fs laser pulses in the case of a spiral scan process can consequently be avoided by a program-correlated blanking or by a purposeful modulation of the pulse power of the laser radiation. In all cases the laser source continues to run undisturbed with fixed and optimised beam parameters such as pulse energy, pulse duration as well as divergence and beam-parameter product, as a result of which the incision quality remains uniformly optimised.

The invention may also be utilised for other fs laser applications in ophthalmology. For example, similar incision schemata may be employed for lamellar and penetrating keratoplasty, such as, for instance, in the case of a lenticular extraction or similar.

The invention claimed is:

1. System for ophthalmic laser surgery, comprising:
a source of pulsed laser radiation;
a scanner for deflecting the laser radiation;
an electronic control unit which has been set up to control the scanner in accordance with a predetermined incision geometry; and
a modulator unit for modulating the laser pulses emitted from the source, the electronic control unit configured to control the modulator unit in accordance with a beam-deflection pattern established for the incision geometry in such a manner that in predetermined parts of the beam-deflection pattern at least some of the laser pulses have a reduced pulse energy relative to a pulse energy of laser pulses for other parts of the beam-deflection pattern, wherein the beam-deflection pattern includes a spiral pattern having an inner spiral region and an outer spiral region and wherein the control unit controls the modulator unit to produce a uniform focal-location density over the spiral pattern by producing an energy reduction of a first ratio of the laser pulses emitted from the source for the inner spiral region and producing an energy reduction of a second ratio of the laser pulses emitted from the source for the outer spiral region, the first ratio being greater than the second ratio.

2. System according to claim 1, wherein the energy reduction of the laser pulses emitted from the source comprises a blanking of the laser pulses such that a pulse-rate of the laser pulses impinging on an eye under treatment are changed in accordance with the following equation:

$$S_f = const \sim \frac{d_i}{f_i} \ldots \frac{d_0}{f_0} f_i << f_0 \text{ as } d_i << d_0$$

where:
$f_i$=pulse-rate in the inner spiral region,
$f_O$=pulse-rate in the outer spiral region,
$s_f$=spot spacing of the spiral pattern,
$d_i$=diameter of a path of the inner spiral region, and
$d_O$=diameter of a path of the outer spiral region.

3. System according to claim 1, wherein the modulator unit includes an acousto-optical or electro-optical modulator.

4. System according to claim 1, wherein the modulator unit includes an optical grating component with variable diffraction efficiency.

5. System according to claim 1, wherein a beam dump is assigned to the modulator unit, wherein the beam dump is configured to absorb laser pulses deflected from the modulator unit.

6. System according to claim 1, wherein the control unit is configured to control the modulator unit in such a manner that the energy reduction of the laser pulses emitted from the source comprises a blanking of the laser pulses.

7. The system of claim 1, wherein the energy reduction of at least some of the laser pulses comprises a blanking of the laser pulses.

8. The system of claim 7, further comprising a beam dump in optical communication with the modulator, the beam dump configured to absorb laser pulses blanked by the modulator.

9. The system of claim 8, wherein the beam dump is configured to absorb the laser pulses blanked by the modulator such that they are removed from a beam path of the laser radiation.

10. The system of claim 7, wherein the modulator is an acousto-optical modulator having a switching time between 2 μs and 10 μs.

11. A system for ophthalmic laser surgery on ocular tissue, the system comprising:
- a source of pulsed laser radiation for making an incision in ocular tissue, the source generating a plurality of laser pulses;
- a modulator unit for modulating the plurality of laser pulses;
- a scanner for deflecting the plurality of laser pulses; and
- an electronic control unit electrically connected to said scanner and electrically connected to said modulator unit, the electronic control unit generating a scanner control signal to control the scanner through at least a first predetermined serpentine deflection pattern having a plurality of line paths extending parallel to one another and with a plurality of reversing bends each terminally connecting a pair of adjacent line paths, wherein the predetermined serpentine deflection pattern is configured to define a planar flap-bed incision and wherein the reversing bends are positioned outside of a desired radius of the flap-bed incision, and the electronic control unit generating a first modulator control signal to control pulse energy of the laser pulse within said line paths and a second modulator control signal to control pulse energy of the laser pulse within said reversing bends, wherein the pulse energy in the second portion is less than the pulse energy in the first portion.

12. The system of claim 11, wherein the modulator unit comprises an optical grating with variable diffraction efficiency.

13. The system of claim 12, wherein the optical grating is in communication with a beam dump such that at least portions of at least some of the laser pulses within the second portion are directed to the beam dump by the optical grating.

14. The system of claim 11, wherein the modulator unit comprises an acousto-optical modulator.

15. The system of claim 11, wherein the modulator unit comprises an electro-optical modulator.

* * * * *